United States Patent [19]

Gunner et al.

[11] Patent Number: 5,057,315

[45] Date of Patent: * Oct. 15, 1991

[54] METHOD AND DEVICE FOR THE BIOLOGICAL CONTROL OF COCKROACHES

[75] Inventors: Haim B. Gunner; Fernando Agudelo-Silva, both of Amherst; Carol A. Johnson, Haydenville, all of Mass.

[73] Assignee: EcoScience Laboratories, Inc., Amherst, Mass.

[ * ] Notice: The portion of the term of this patent subsequent to Oct. 15, 2008 has been disclaimed.

[21] Appl. No.: 324,461

[22] Filed: Mar. 15, 1989

[51] Int. Cl.$^5$ .................. A01N 63/00; A01N 25/00; A01M 1/00

[52] U.S. Cl. ..................... 424/93; 424/405; 424/DIG. 8; 43/132.1

[58] Field of Search ............... 424/405, 93; 43/132.1, 43/121

[56] References Cited

U.S. PATENT DOCUMENTS

| | | | |
|---|---|---|---|
| D. 269,290 | 6/1983 | Carlsen | D22/19 |
| D. 275,124 | 8/1984 | Carlsen | D22/19 |
| D. 278,842 | 5/1985 | Woodruff | D22/19 |
| 3,337,395 | 8/1967 | Page | 424/405 |
| 3,851,417 | 12/1974 | Wunsche | 43/121 |
| 3,908,302 | 9/1975 | Carr | 43/121 |
| 3,913,259 | 10/1975 | Nishimura et al. | 43/114 |
| 3,931,692 | 1/1976 | Hermanson | 43/131 |
| 3,940,874 | 3/1976 | Katsuda | 43/114 |
| 4,030,233 | 6/1977 | Wunsche | 43/121 |
| 4,152,862 | 5/1979 | Mohiuddin | 43/121 |
| 4,173,093 | 11/1979 | Nakai | 43/121 |
| 4,208,828 | 6/1980 | Hall et al. | 43/114 |
| 4,316,344 | 2/1982 | Carlsen | 43/114 |
| 4,395,842 | 8/1983 | Margulies | 43/114 |
| 4,400,905 | 8/1983 | Brown | 43/132.1 |
| 4,411,094 | 10/1983 | Spackova et al. | 43/121 |
| 4,423,564 | 1/1984 | Davies et al. | 43/121 |
| 4,563,836 | 1/1986 | Woodruff et al. | 43/131 |
| 4,608,774 | 9/1986 | Sherman | 43/114 |
| 4,642,935 | 2/1987 | Fierer | 43/121 |
| 4,696,127 | 9/1987 | Dobbs | 43/121 |
| 4,709,502 | 12/1987 | Bierman | 43/112 |
| 4,921,703 | 5/1990 | Higuchi | 424/419 |

OTHER PUBLICATIONS

Archbold et al., *Environ. Entomol.* 15(1), 221–226 (1986).

Strand and Brooks, Pathogens of Medically Important Arthropods, Roberts & Strand, editors *Bulletin of the World Health Organization* 55(Supp. No. 1), pp. 289–304, (Boyce Thompson Inst., Yonkers, NY 10701).

Ryan and Nicholas, *J. Inveterbrte Path.* 19, 299–307 (1972).

Appel et al., *Comp. Biochem. Physiol. A. Comp. Physiol.* 88(3), 491–494 (1987).

Verrett et al., *J. Econ. Entomol.* 80(6), 1205–1212 (1987).

Archbold et al., *J. Med. Entomol.* 24(2), 269–272 (1987).

Gunnarsson, S. G. S., *J. Invertebr. Pathol.* (46)3, 312–319 (1985).

Lin et al., *Natural Enemies of Insects* 9(3), 168–172 (1987).

*Primary Examiner*—John W. Rollins
*Assistant Examiner*—R. Gitomer
*Attorney, Agent, or Firm*—Kilpatrick & Cody

[57] ABSTRACT

A convenient, economical, non-toxic and effective method and means for the control of roaches by administration of entomopathogenic fungi to the cockroaches. In the preferred embodiment, the roaches are exposed to the fungi by means of a contamination chamber having openings through which the cockroaches enter and come in contact with a living culture of a fungus which is pathogenic to cockroaches. The fungal spores attach to the roach, germinate and penetrate into the body of the cockroach, resulting in the death of the infected roach. Death takes approximately two to three weeks after contact with the culture. During this time, the infected roach disseminates spores of the pathogenic fungus throughout the infested areas which may subsequently infect other roaches. Given the proper environmental conditions, the fungus sporulates on the cadaver of the roach and the conidia can be transmitted to other cockroaches, resulting in a further spread of the disease.

6 Claims, 2 Drawing Sheets

METHOD AND DEVICE FOR THE BIOLOGICAL CONTROL OF COCKROACHES

BACKGROUND OF THE INVENTION

The present invention is generally in the field of biological control of insect pests, specifically in the area of use of entomopathogenic fungi for the control of cockroaches.

*Blattella germanica* (the German cockroach) and *Periplaneta americana* (the American cockroach) are ubiquitous throughout the world. They are the major insect pests in residences, restaurants, hospitals, dormitories and warehouses. Cockroaches are unsightly and have been implicated as vectors of several human disease agents.

The most common means of roach control is the regular spraying of chemical insecticides. Not only are these insecticides expensive, but their long term effects on the inhabitants of the places in which they are used, as well as the environment, are unknown in most cases and potentially hazardous. Further, there is a tendency among the treated insects for resistant strains to develop, which requires the use of large quantities and different chemicals to treat.

Insect pathogens are a possible alternative to the common use of highly toxic chemical insecticides for the control of insect pests. Fungi are one of the promising groups of insect pathogens suitable for use as biological agents for the control of insects.

Fungi are found either as single cell organisms or as multicellular colonies. While fungi are eukaryotic and therefore more highly differentiated than bacteria, they are less differentiated than higher plants. Fungi are incapable of utilizing light as an energy source and therefore restricted to a saprophytic or parasitic existence.

The most common mode of growth and reproduction for fungi is vegetative or asexual reproduction which involves sporulation followed by germination of the spores. Asexual spores, or conidia, form at the tips and along the sides of hyphae, the branching filamentous structures of multicellular colonies. In the proper environment, the conidia germinate, become enlarged and produce germ tubes. The germ tubes develop, in time, into hyphae which in turn form colonies.

The fungus *Metarhizium anisopliae* is an example of a fungus that infects certain species of insects. This fungus has been administered to insect pests by a number of methods, including direct spraying, injection, and by the application of the fungus to the plant material on which the insect lives or feeds. In some insect species, infection with the fungus has been shown to result in death. In one species, infected individuals were able to transmit the fungus to non-infected members of their colony.

To date, the majority of work evaluating entomopathogenic fungi for biological control of insect pests has focused on applications involving agriculturally important insect pests and mosquitoes. *Metarhizium anisopliae* is one of the most widely studied fungus for biological control of insects. However, there are few reports which address the ability of *M.anisopliae* to infect cockroaches. Gunnarsson, S.G.S., *J. Invertebr. Pathol.* (46)3, 312-319, (1985), for example, has shown that *Periplaneta americana* exhibits a defense reaction (nodule formation) to the injection of *M. anisopliae* conidia. However, no mention of the potential of the fungus for roach control was made. In fact, it can be implied from the data that the American cockroach has a strong defense to injected *M. anisopliae* spores. Further, there are a number of insect species which are not infected by contact with entomopathogenic fungi.

No one has yet developed a consistent and commercially viable way of infecting insects and assuring that the fungi are dispersed throughout the breeding populations. For example, with reference to cockroaches, it is clearly impractical to use a method such as the one referenced above requiring inoculation of individual insects with the fungi.

As of this time, there has been no successful demonstration by others of the practical, reliable and economical employment of an entomopathogenic fungus for the management and biological control of insects infesting houses or buildings.

It is therefore an object of the present invention to biologically control cockroaches using entomopathogenic fungi.

It is a further object of the present invention to provide a device for the convenient, reliable and economically feasible application of fungi in the biological control of cockroaches.

It is a further object of the present invention to provide a method and means for infecting all cockroaches in a breeding colony by dissemination of fungi pathogenic for cockroaches.

It is another object of the present invention to provide a method and means for infection and killing of cockroaches by a variety of fungi so that development of resistant strains is avoided.

SUMMARY OF THE INVENTION

A method for control and extermination of roaches using the dissemination of entomopathogenic fungi including, for example, *Metarhizium anisopliae* and *Beauveria bassiana*. The fungi which are effective are those which have infective structures that have the appropriate biochemical mechanisms, which may include recognition of cockroach cuticle, to initiate the infection process in cockroaches. The fungi are applied to the environment to be treated using means which insure contact and infection of the roaches with the fungi.

In the preferred embodiment for the biological control of cockroaches, a contamination chamber is used for the administration of entomopathogenic fungi to the cockroaches. The device consists of a closed chamber having entrances for the cockroaches and contains a living culture of a fungus pathogenic to cockroaches. The geometry of the device is such that upon entering the chamber the cockroach comes in contact with the culture of the pathogenic fungus.

The contamination chambers are placed in habitats frequented by cockroaches. In the most preferred embodiment, the culture medium for the fungus is also attractive to the cockroaches, so that while the cockroaches are out foraging, they enter the chamber in search of food, then rub against the fungus as they explore, and, optionally, consume, the fungal culture. In so doing, the roaches contact the fungal conidia which attach to the surface of the cockroach (integument). After attachment, the conidia germinate on the integument and the germ tubes of the germinating conidia penetrate the cuticle of the cockroach. The germ tubes continue to penetrate through the cuticle of the cockroach until they reach the internal body cavity (hemocoel) of the insect, thereby killing the roach.

DETAILED DESCRIPTION OF THE INVENTION

The devices described below provide a convenient, non-toxic and reliable method for the administration of entomopathogenic fungi in an economical and cost-effective fashion. The small, lightweight contamination chambers are unobtrusive and are easily placed in locations of heavy insect infestation, increasing the efficacy of the device. Because the devices provide an environment within which the fungus can flourish over extended periods of time, a single device is effective for a longer period of time than with other methods, such as spraying, where effectiveness of the agent dissipates over a short time. The longevity of the devices also decreases the number of applications and maintenance time required for effective treatment. Another advantage of the devices is that they are constructed of readily available and relatively inexpensive materials, which insures an abundant supply of cost-effective devices.

The method for killing cockroaches, especially American and German varieties, as well as others, is based on the observed pathogenesis of at least two different genera of fungi (three strains) on roaches infected by contact with a living culture, either consisting of a nutrient culture inoculated with the fungi, or the corpse of another roach that has died from infection with the fungi.

In a preferred embodiment, the roaches are infected by exposure to the fungus in small chambers having apertures through which the cockroaches enter and exit. A cockroach enters the chamber either as the result of general exploration or as the result of being lured inside the device by the action of cockroach attractant (such as food sources or pheromones). Once inside the chamber the cockroach comes in contact with the entomopathogenic fungus. The conidia of the pathogen attach to the body of the cockroach. The infected cockroach leaves the chamber and returns to its harboring sites. While dispersing from the contamination chamber to other sites, conidia attached to the roaches integument can be dislodged and may contaminate the habitat, thereby exposing additional cockroaches to infection.

After the cockroach dies and the fungal mycelium sporulates on the body of the insect, other cockroaches can be infected by exposure to the conidia produced on the dead insect. Exposure of the infected roach after the fungus sporulates on the dead body of the infected roach effectively transmits the pathogen to other noninfected cockroaches. This leads to the death or dispersal of the remainder of the colony.

Figure 1:
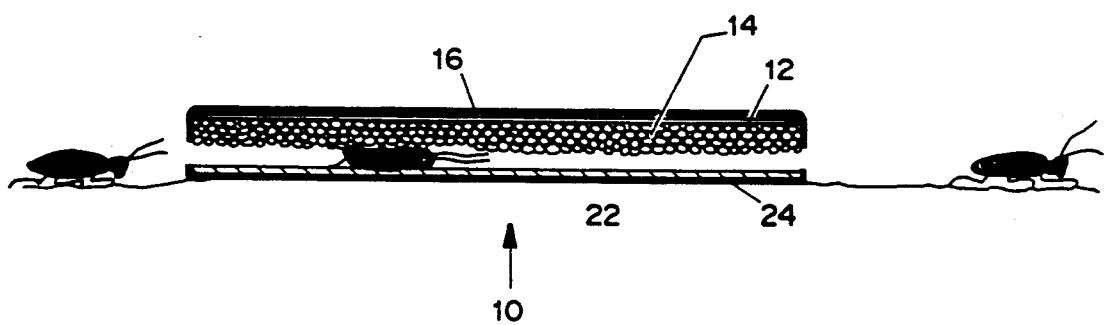
FIG. 1 is a cross-sectional view of a contamination chamber for infection of roaches by entomopathogenic fungi, consisting of a culture of fungus deposited as a mat on a nutrient-containing agar ceiling and a floor with a sterile polystyrene pad to maintain the humidity within the chamber. The two opposing surfaces are separated by a space of 2 to 3 mm through which the cockroach travels and experiences a tigmotactic response.

As diagrammed in FIG. 1, a contamination chamber 10 can be constructed by pouring 50 ml of culture medium 12 for the fungus 14 into a dish 16, for example, a 100×15 mm plastic petri dish. An example of a useful culture medium consists of 1% dextrose, 1% yeast extract, 5% rice flour, 1.5% agar and 0.5% 5x Dubois sporulation salts. The 5x Dubois sporulation salts consists of 15 g $(NH_4)_2SO_4$/1000 ml; 0.30 g $MgSO_4 \cdot 7H_2O$/1000 ml; 0.15 g $MnSO_4 \cdot H_2O$/1000 ml; 0.0375 g $CuSO_4 \cdot 5H_2O$/1000 ml; 0.0375 g $ZnSO_4 \cdot 7H_2O$/1000 ml; and 0.0038 g $FeSO_4 \cdot 7H_2O$/1000 ml. Each salt is completely dissolved before the next salt is added and the solution is autoclaved. Other useful culture mediums are known, or can be optimized from those that are known, by those skilled in the art.

Figure 2:
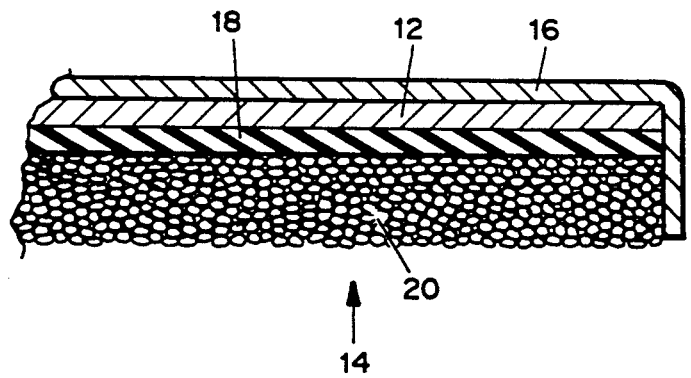
FIG. 2 is an enlarged cross-sectional view of the chamber of FIG. 1 containing 50 ml of fungal culture media and inoculated with an entomopathogenic fungus which has formed a mat of hyphae and conidia (spores).

After solidification, the culture medium is inoculated with spores of the appropriate fungal pathogen (inoculation is accomplished by streaking the surface of the medium with an inoculating loop carrying fungal spores). As shown in FIG. 2, after seven days of growth at 28° C. with 75% relative humidity, the fungus 14 will have produced a thick layer of mycelia 18 and conidia 20 that cover the surface of the culture medium 12. The dish 16 is then inverted so that the culture medium 12 with the fungal growth 14 is now the ceiling of the chamber 10.

In this example, a sterile polystyrene pad 22 is placed in the bottom 24 of the chamber 10. The inverted chamber 10 has a 2–3 mm space between the surface of the sporulated fungus 26 on the ceiling of the chamber and the polystyrene floor 22 of the chamber. As depicted in FIG. 1, this forces the roaches to come in contact with the fungus as they pass through the chamber 10.

Figure 3:
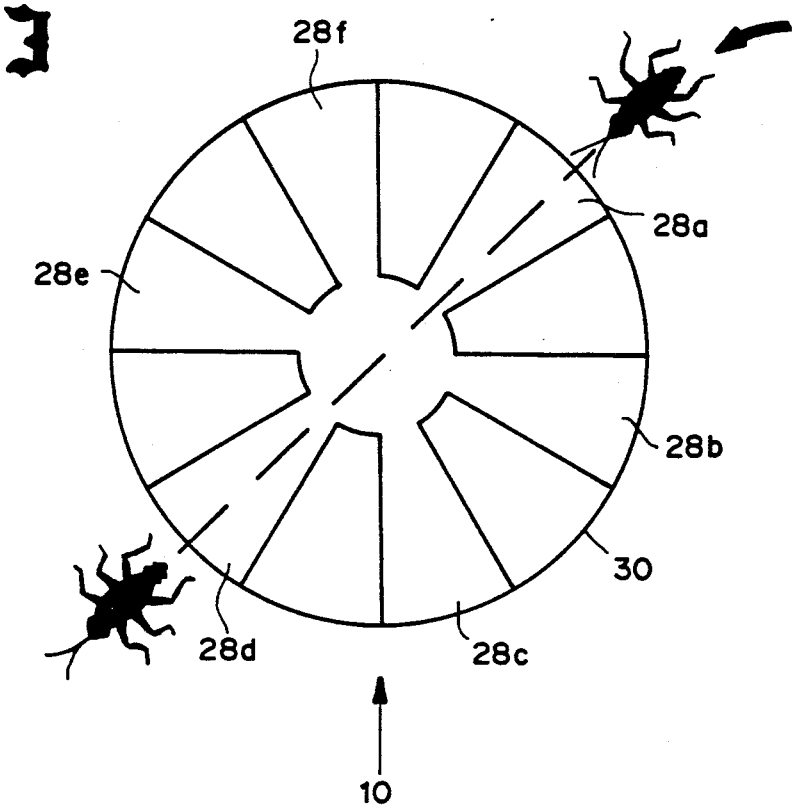
FIG. 3 is a cross-sectional view of the top of the chamber of FIG. 1 showing the openings spaced equidistantly around the perimeter.

The chamber 10 is shown in cross-section in FIG. 3. Openings 28a–28f are made on the perimeter 30 of the chamber 10, each opening being 9 mm square and equidistantly spaced around the perimeter of the contamination chamber. The size of the openings is proportional to the size of the insect. For example, larger openings are used for control of large species of cockroaches, such as the Oriental cockroach. When the chambers are placed in habitats infested with cockroaches, the latter enter the chamber through the openings, where they are forced into contact with the fungal spores.

The following non-limiting examples demonstrate the efficacy of the contamination chambers in controlling cockroaches, using both German (*Blattella germanica*) and American cockroaches (*Periplaneta americana*) in the tests. In all cases the cockroach populations were significantly reduced by the fungus present in the contamination chambers.

EXAMPLE 1

Infection and Death of *Blattella germanica* with *Metarhizium anisopliae* Strain PA-2

The study utilized a plastic container in the shape of a box (6×12×4 in) to hold the cockroaches. The lid had ten circular ventilation holes (⅜ inch diameter). The holes were screened with insect netting to prevent the escape of insects and the accumulation of moisture. Three different stages of *Blattella germanica* (German cockroach) development were studied: immature cockroaches at the third instar stage, immature cockroaches at the sixth instar stage, and adult insects. Twenty insects, 10 males and 10 females of each developmental stage, were studied per box. Each developmental stage was studied in duplicate. Controls, exposed to contamination chambers without fungus, were utilized to determine normal cockroach mortality for each stage.

One contamination chamber was placed in one end of each box. The chamber was placed in such a manner that the fungus was on the ceiling of the chamber. The side apertures of the chamber were open so that the cockroaches could enter the device. Food, Purina ® lab chow, and water for the roaches were placed on the other end of the box.

When the cockroaches entered the contamination chamber, the conidia of the fungus attached to the roaches, the conidia germinated and invaded the body of the cockroach, and the roaches died.

The mortality of the roaches was tallied every week for six weeks. The results of this study are presented in Table 1 and clearly demonstrate the efficacy of the devices for all of the developmental stages of the German cockroach.

TABLE 1

| Weeks After Exposing the Roaches to the Contamination Chamber | % Death of Roaches infected with *M. anisopliae*. Strain PA-2 Percent Cockroach Survival Developmental Stage | | |
|---|---|---|---|
| | Third | Sixth | Adult |
| 2 | 85 | 95 | 80 |
| 3 | 80 | 60 | 60 |
| 4 | 60 | 45 | 45 |
| 6 | 15 | 10 | 5 |

Survival of the control population of cockroaches was greater than 90 percent. This strain of fungus, *Metarhizium anisopliae* Strain PA-2, was originally selected by exposing cockroaches to *Metarhizium anisopliae*, isolating the fungus from dead cockroaches and culturing the fungus in artificial culture medium.

EXAMPLE 2

Long Term Killing of Roaches by Fungal Contamination and Infection

This study demonstrates that the devices of the present invention are effective in maintaining an active entomopathogenic fungal culture over a long period of time and that the fungal spores in the contamination chamber remain infective to cockroaches for many weeks. From a practical perspective, the importance of this study is that it demonstrates that the chambers are useful over a commercially acceptable period.

As in the preceding study, contamination chambers were placed in plastic boxes containing cockroaches at different developmental stages. At the third week and sixth week, the contamination chambers were transferred to fresh boxes containing 20 different (uninfected) German cockroaches of the corresponding developmental stage. Cockroach mortality in each box in which a chamber was placed was tallied at weekly intervals for six weeks. The results of this study appear in Table 2.

TABLE 2

| Effective Lifetime of Contamination Chambers. | | | | |
|---|---|---|---|---|
| Age of Chamber Weeks | Weeks After Exposure to Chamber | % Cockroach Survival Instar Exposed | | |
| | | III | VI | Adults |
| 0 | 2 | 95 | 90 | 98 |
| | 3 | 80 | 23 | 73 |
| | 4 | 60 | 10 | 50 |
| | 6 | 58 | 10 | 3 |
| 3 | 2 | 95 | 80 | 83 |
| | 3 | 90 | 30 | 58 |
| | 4 | 85 | 18 | 40 |
| | 6 | 58 | 3 | 18 |
| 6 | 2 | 88 | 65 | 55 |
| | 3 | 88 | 45 | 45 |
| | 4 | 60 | 10 | 10 |
| | 6 | 13 | 5 | 0 |

The survival of control cockroaches in all cases was greater than 90 percent.

As it can be concluded from this study, the effectiveness of the contamination chamber in reducing roach populations was the same when the chambers were freshly made (age 0 weeks) as when the chambers were three to six weeks old. For example, sixth instar roaches, after being exposed to six week old chambers, exhibited essentially the same percent survival as roaches exposed to new chambers (0 weeks old). These results establish that the chambers maintain their killing power for greater than six weeks, indicating that the chambers can be used to significantly reduce roach populations for at least six weeks.

EXAMPLE 3

Effectiveness of the Addition of a Roach Attractant to the Contamination Chamber This study was to ascertain whether the effectiveness of the contamination chamber killing cockroaches could be improved by introducing a cockroach attractant into the chamber. Two attractants were tested, banana extract and Purina ® laboratory chow. The attractants were placed on the floor of the contamination chamber.

Figure 4:
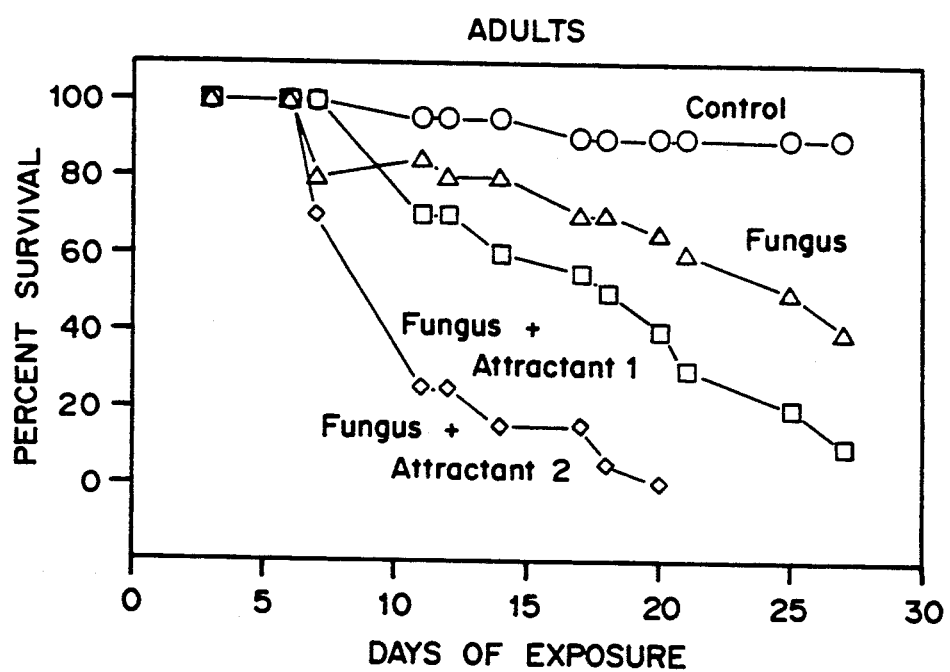
FIG. 4 is a graph of the mortality of cockroaches (% survival) as a function of time after exposure (days). Studies of cockroach mortality were conducted without pathogenic fungus (—O—O—), with the entomopathogenic fungus *M. anisopliae* but without attractant (—Δ—Δ—), with *M. anisopliae* and the attractants (1) banana extract (—□—□—), and with *M. anisopliae* and (2) Purina ® lab chow (—<>—<>—).

The methodology followed for this study is as outlined in Examples 1 and 2, with results shown for adult German cockroaches in FIG. 4. The results establish that the addition of a cockroach attractant to contamination chambers further increases cockroach mortality relative to chambers to which no attractant had been added.

EXAMPLE 4

Infection and Death of *Periplaneta americana* with *Metarhizium anisopliae* Strain PA-2

The methodology for this study is similar to that utilized for the studies of examples 1, 2, and 3, except that *Periplaneta americana* (American cockroach) were used as the test insects and moist sponges were placed in the boxes to provide a higher relative humidity, enhancing the activity of the fungus on the cockroaches.

The results are shown in Table 3.

TABLE 3

Effect of *M. anisopliae* strain PA-2 infection on survival of *periplaneta americana*.

| Weeks After Exposing the Cockroaches to the Chamber | Percent Cockroach Survival (%) |
|---|---|
| 1 | 70 |
| 2 | 25 |
| 3 | 15 |

The survival of control roaches was greater than 90 percent.

The preceding studies demonstrated that, using the appropriate device, cockroaches can be infected with a strain of *M. anisopliae* that had been selected after passage through cockroaches. The following studies demonstrate that other entomopathogenic fungi can be used in the contamination chamber to kill cockroaches.

EXAMPLE 5

Infection and Death of *Blattella germanica* (German cockroach) with another *M. anisopliae* strain and *Beauveria bassiana*

This study utilized different potential pathogenic fungi, *Beauveria bassiana* and *Paecilomyces farinosus* strain 38 F-6, as well as a second strain of *M. anisopliae*, in the contamination chambers. Other details of this study are as described above for Example 1, using German cockroaches.

As established by the results shown in Table 4 and Table 5, *Beauveria bassiana*, as well as at least one other strain of *M. anisopliae*, are effective at infecting and killing both German and American cockroaches at the sixth instar and adult stages. However, at least one other strain of fungus, *Paecilomyces farinosus* strain 38 F-6, was not pathogenic for roaches under these conditions.

TABLE 4

Infection and Death of *Blattella germanica* (German cockroach) with *M. anisopliae* strain PA-2, *M. anisopliae* strain 1958, *Beauveria bassiana* strain 252 F-9, and *Paecilomyces farinosus* strain 38 F-6.
Percent Cockroach Survival (VI-Instar)

| Days After Exposing Cockroaches to the Chamber | Control | Fungal Strain | | | | |
|---|---|---|---|---|---|---|
| | | Ma PA-2 | Ma RS-703 | Ma 1958 | Bb 252 F-9 | Pf 38 F-6 |
| 1 | 100 | 100 | 100 | 100 | 100 | 100 |
| 4 | 100 | 100 | 100 | 100 | 100 | 100 |
| 13 | 95 | 90 | 75 | 75 | 80 | 90 |
| 20 | 95 | 40 | 65 | 40 | 75 | 90 |
| 26 | 95 | 25 | 50 | 25 | 45 | 90 |
| 29 | 95 | 50 | 15 | 15 | 40 | 85 |

Ma PA-2: *M. anisopliae* strain PA-2
Ma RS-703: *M. anisopliae* strain RS-703
Ma 1958 *M. anisopliae* strain 1958
Bb 252 F-9: *Beauveria bassiana* strain 252 F-9
Pf 38 F-6: *Paceilomyces farinosus* strain 38 F-6

From this study, it is clear that Ma Pa-2, Ma RS-703, Ma 1958 and Bb 252 F-9 significantly reduced cockroach survival when cockroaches are infected at the sixth instar stage. It is equally clear that another entomopathogenic fungus, *P. farinosus*, was not effective in killing significant numbers of immature roaches.

Some of the isolates that were found to be infective to sixth instar cockroaches were also infective against adult cockroaches, as shown in Table 5.

TABLE 5

Infection and Death of *Blattella germanica* (German cockroach) with *M. anisopliae* strain PA-2, *M. anisopliae* strain 1958, *Beauveria bassiana* strain 252 F-9
Percent Cockroach Survival (Adults)

| Days After Exposing Cockroaches to the Chamber | Control | Fungal Strain | | | | | |
|---|---|---|---|---|---|---|---|
| | | Ma PA-2 | Ma RS-703 | Ma 1958 | Bb 252 F-9 | Bb 533-10 | Pf 38 F-6 |
| 1 | 100 | 100 | 100 | 100 | 100 | 100 | 100 |
| 4 | 100 | 100 | 100 | 100 | 100 | 100 | 100 |
| 13 | 100 | 100 | 100 | 100 | 95 | 95 | 100 |
| 20 | 100 | 90 | 100 | 85 | 95 | 100 | 95 |
| 26 | 100 | 45 | 100 | 35 | 65 | 100 | 90 |
| 29 | 100 | 30 | 90 | 30 | 60 | 100 | 90 |

It can be concluded that Ma PA-2, Ma 1958 and Bb 252 F-9 reduce survival of adult cockroaches.

In general, it is believed that the high efficacy of the method of the present invention for controlling cockroaches results from the use of a chamber that exposes the cockroaches to massive dosages of an entomopathogenic fungus in combination with the selection of the fungus from a group of normally soil-dwelling entomopathogenic fungi, to which cockroaches are not normally exposed.

There appear to be several reasons for the differences in pathogenicity to cockroaches of the various fungal strains that can be employed:

a. Specificity of attachment and germination of fungal conidia to cockroach cuticle Entomopathogenic fungi exhibit differential ability to germinate on insect cuticles. It is likely that the above-described highly virulent fungi, *M. anisopliae* strains Pa-2 and 1958 and *B. bassiana* strain 252 F-9, find the proper stimuli on the cockroach cuticle to attach and germinate. Nonvirulent strains such as *P. farinosus* 38 F-6 may not find the proper attachment and germination stimuli on the cockroach's cuticle.

b. Defense reactions of the cockroaches to invading fungal hyphae

Alternatively, or in addition, it may be that the host's humoral and cellular defenses are overcome by those fungi demonstrating virulence, but not by the non-virulent fungi.

c. Differences between sporulating structures of the fungi

Another mechanism may be the production of spores by the most virulent fungi in such a manner that the spores are easily dislodged by the cockroaches when they enter into the chamber, the result being massive exposure of the cockroaches to fungal inoculum, leading to lethal infection. In contrast, strains of non-virulent fungi may sporulate in such a way that their conidia are not easily dislodged when roaches enter the chamber and rub against the conidia, leading to in a non-lethal infection.

Other strains of virulent fungi can be isolated by screening fungi for their response to various elements on the cockroach cuticle, such as soluble substances that enhance attachment and conidia germination. This selective screening provides a method for developing useful pathogen/host systems, thereby increasing the number of fungi that can be used for roach control in the contamination chamber.

The above detailed examples of the present invention demonstrate the feasibility of the administration of entomopathogens to cockroaches through contact association in the disclosed contamination chambers. The present invention provides an economical, practical, environmentally compatible, and efficient means for the biological control of cockroaches. Modifications and variations of the present invention will be obvious to those skilled in the art from the foregoing detailed description. Such modifications and variations are intended to come within the scope of the appended claims.

I claim:

1. A method for controlling roaches comprising providing a fungus that can be pathogenic to the roaches to be controlled in a chamber including a nutrient medium for the fungus, the chamber containing and maintaining an effective density of the fungus to infect the roaches, being attractive to roaches, and having a geometry or shape including apertures for the roaches which forces the roaches into contact with an effective amount of the fungus to lethally infect the roaches with the fungus.

2. The method of claim 1 wherein the pathogenic fungus is selected from the group of *Metarhizium anisopliae, Beauveria bassiana,* and combinations thereof.

3. The method of claim 1 further comprising a moisture retaining pad for maintaining humidity in the chamber of the conidia of the pathogenic fungus to respond to particular stimuli from, and affinities for, the cuticle of roaches.

4. The method of claim 1 further comprising providing an attractant for roaches.

5. The method of claim 4 wherein the attractant is selected from the group consisting of pheromones and roach foods.

6. The method of claim 1 further comprising providing means for maintaining the fungus in a humid environment.

* * * * *